US008788216B2

(12) United States Patent
Mizumoto et al.

(10) Patent No.: US 8,788,216 B2
(45) Date of Patent: Jul. 22, 2014

(54) URINE SAMPLE TESTING APPARATUS AND APPARATUS FOR PROCESSING MEASUREMENT RESULT OF URINE SAMPLE

(75) Inventors: Toru Mizumoto, Kobe (JP); Keisuke Tsutsumida, Kobe (JP); Takayoshi Izumi, Kobe (JP)

(73) Assignee: Sysmex Corporation, Kobe-Shi, Hyogo (JP)

( * ) Notice: Subject to any disclaimer, the term of this patent is extended or adjusted under 35 U.S.C. 154(b) by 369 days.

(21) Appl. No.: 13/194,167

(22) Filed: Jul. 29, 2011

(65) Prior Publication Data
US 2012/0035879 A1 Feb. 9, 2012

(30) Foreign Application Priority Data
Aug. 3, 2010 (JP) ................................. 2010-174191

(51) Int. Cl.
*G01N 35/00* (2006.01)
*C12M 1/34* (2006.01)

(52) U.S. Cl.
USPC ............................................. 702/23; 702/30

(58) Field of Classification Search
USPC ................ 702/22, 23, 25, 26, 30–32; 436/50
See application file for complete search history.

(56) References Cited

U.S. PATENT DOCUMENTS

| 5,851,487 A | 12/1998 | Katayama et al. |
| 2007/0072301 A1* | 3/2007 | Fukuda et al. ................. 436/50 |

* cited by examiner

*Primary Examiner* — Manuel L Barbee
(74) *Attorney, Agent, or Firm* — Brinks Gilson & Lione

(57) ABSTRACT

A urine sample testing apparatus comprises: a urine qualitative measuring section configured to acquire a measurement result for each of a plurality of urine qualitative measurement items; a urine sediment measuring section configured to acquire a measurement result for each of a plurality of urine sediment measurement items; an operation part that is operable by a user to specify a combination of one of the plurality of urine qualitative measurement items and one of the plurality of urine sediment measurement items; an information processing unit configured to determine whether or not a first measurement result of the urine sample obtained by the urine qualitative measuring section and a second measurement result of the urine sample obtained by the urine sediment measuring section have a predetermined relationship with respect to the urine qualitative measurement item and the urine sediment measurement item included in the specified combination.

19 Claims, 13 Drawing Sheets

FIG. 4

| NUMBER (F11) | USE FLAG (F12) | DISPLAY FLAG (F13) | URINE QUALITATIVE TEST ITEM (F14) | URINE SEDIMENT TEST ITEM (F15) |
|---|---|---|---|---|
| 1 | 1 | 1 | BLD | RBC |
| 2 | 0 | 0 | LEU | WBC |
| 3 | 1 | 1 | PRO | CAST |
| ⋮ | ⋮ | ⋮ | ⋮ | ⋮ |

T1

| CROSS CHECK TARGET ITEM (F21) | CROSS CHECK TABLE INFORMATION (F22) |
|---|---|
| BLD×RBC | 0000111⋯ |
| LEU×WBC | 0000001⋯ |
| PRO×CAST | 0001110⋯ |
| ⋮ | ⋮ |

```
┌─ RANK VALUE ──────────────────┐
│  ┌─────────┐                  │
│  │ RBC   ▼ │                  │
│  └─────────┘                  │
│  RANK                         │
│    1    <=    ┌────────6─┐ [/uL]
│    2    <=    ┌───────17─┐ [/uL]
│    3    <=    ┌───────28─┐ [/uL]
│    4    <=    ┌───────55─┐ [/uL]
│    5    <=    ┌──────110─┐ [/uL]
│    6    <=    ┌──────275─┐ [/uL]
│    7    <=    ┌──────550─┐ [/uL]
│    8    <=    ┌────────0─┐ [/uL]
│    9     >    ┌────────0─┐ [/uL]
└───────────────────────────────┘
```

C21 → RBC dropdown
D2 → outer box
C22 → value input fields

FIG. 12

URINE SAMPLE TESTING APPARATUS AND APPARATUS FOR PROCESSING MEASUREMENT RESULT OF URINE SAMPLE

RELATED APPLICATIONS

This application claims priority under 35 U.S.C. §119 to Japanese Patent Application No. 2010-174191 filed on Aug. 3, 2010, the entire content of which is hereby incorporated by reference.

BACKGROUND OF THE INVENTION

1. Field of the Invention

The present invention relates to a urine sample testing apparatus and an apparatus for processing measurement results of a urine sample.

2. Description of the Related Art

A urine qualitative analyzer and a urine sediment analyzer are widely known as an analyzer used for urine testing. U.S. Patent Publication No. 2007/072301 discloses a measurement result check device for mutually checking a measurement result obtained by the urine qualitative analyzer and a measurement result obtained by the urine sediment analyzer, and evaluating the reliability of such measurement results. The measurement result check device is configured to carry out mutual check of measurement results obtained by the urine qualitative analyzer and the urine sediment analyzer for combinations of measurement items set in advance, that is, a combination of occult blood concentration and red blood cell concentration, a combination of white blood cell concentration and white blood cell concentration, a combination of protein concentration and cylinder concentration, a combination of nitrite salt concentration and bacteria concentration, and a combination of specific gravity and conductivity.

However, according to the measurement result check device described in U.S. Patent Publication No. 2007/072301, the check of the measurement result is carried out only for the combinations of the measurement items set in advance in the device, and the measurement result cannot be checked for a combination of measurement items that have not been set. Therefore, it is difficult to flexibly respond to the user's desire to check a new combination of measurement items.

In view of such situations, it is a main object of the present invention to provide an apparatus which allows the user to check a new combination of measurement items easily according to the user's desire.

SUMMARY OF THE INVENTION

The scope of the present invention is defined solely by the appended claims, and is not affected to any degree by the statements within this summary.

A first aspect of the present invention is a urine sample testing apparatus comprising: a urine qualitative measuring section configured to measure a urine sample and acquire a measurement result for each of a plurality of urine qualitative measurement items; a urine sediment measuring section configured to measure the urine sample and acquire a measurement result for each of a plurality of urine sediment measurement items; an operation part that is operable by a user to specify a combination of one of the plurality of urine qualitative measurement items and one of the plurality of urine sediment measurement items; an information processing unit configured to determine whether or not a first measurement result of the urine sample obtained by the urine qualitative measuring section and a second measurement result of the urine sample obtained by the urine sediment measuring section have a predetermined relationship with respect to the urine qualitative measurement item and the urine sediment measurement item included in the combination specified through the operation part; and an output unit configured to output a determination result by the information processing unit.

According to this configuration, the degree of freedom of the combination of the measurement items can be enhanced at the time of checking the measurement results. The combination of the measurement items used to check the measurement results thus can be easily extended according to the request of the user. Furthermore, when information for assisting the diagnosis is obtained from the measurement results of two measurement items and not only the check on the reliability of the measurement result, information can be acquired for the combination of measurement items desired by the user. Thus, each measurement result can be utilized more advantageously than one in the prior art.

A second aspect of the present invention is an apparatus for processing a measurement result of a urine sample comprising: a measurement result acquiring unit configured to acquire a measurement result of a urine sample for each of a plurality of urine qualitative measurement items from a urine qualitative measuring section and acquire a measurement result of the urine sample for each of a plurality of urine sediment measurement items from a urine sediment measuring section; an operation part that is operable by a user to specify a combination of one of the plurality of urine qualitative measurement items and one of the plurality of urine sediment measurement items; an information processing unit configured to determine whether or not a first measurement result of the urine sample obtained by the urine qualitative measuring section and a second measurement result of the urine sample obtained by the urine sediment measuring section have a predetermined relationship with respect to the urine qualitative measurement item and the urine sediment measurement item included in the combination specified through the operation part; and an output unit configured to output a determination result by the information processing unit.

BRIEF DESCRIPTION OF THE DRAWINGS

FIG. 4 is a schematic view showing a configuration of a cross check set value database;

FIG. 7 is a view showing one example of a cross check setting dialogue;

FIG. 9 is a view showing one example of a rank value setting dialogue;

FIG. 12 is a view showing one example of a measurement result screen.

DETAILED DESCRIPTION OF THE PREFERRED EMBODIMENTS

The preferred embodiment of the present invention will now be described below with reference to the drawings.

The present embodiment relates to a clinical sample analyzer for carrying out test of urine protein, urinary sugar or the like (urine qualitative test) and test of red blood cells, white blood cells, epidermal cells, and the like contained in the urine (urine sediment test). The urine sediment test is carried out on the sample determined that further test on the urine sediment is necessary as a result of the urine qualitative test. In the present embodiment, a plurality of sample containers containing different samples is set in a rack, and the rack is set in the sample analyzer to test each sample.

[Configuration of Urine Sample Testing Apparatus]

A urine sample testing apparatus according to the present embodiment will be hereinafter described with reference to the drawings.

Figure 1:
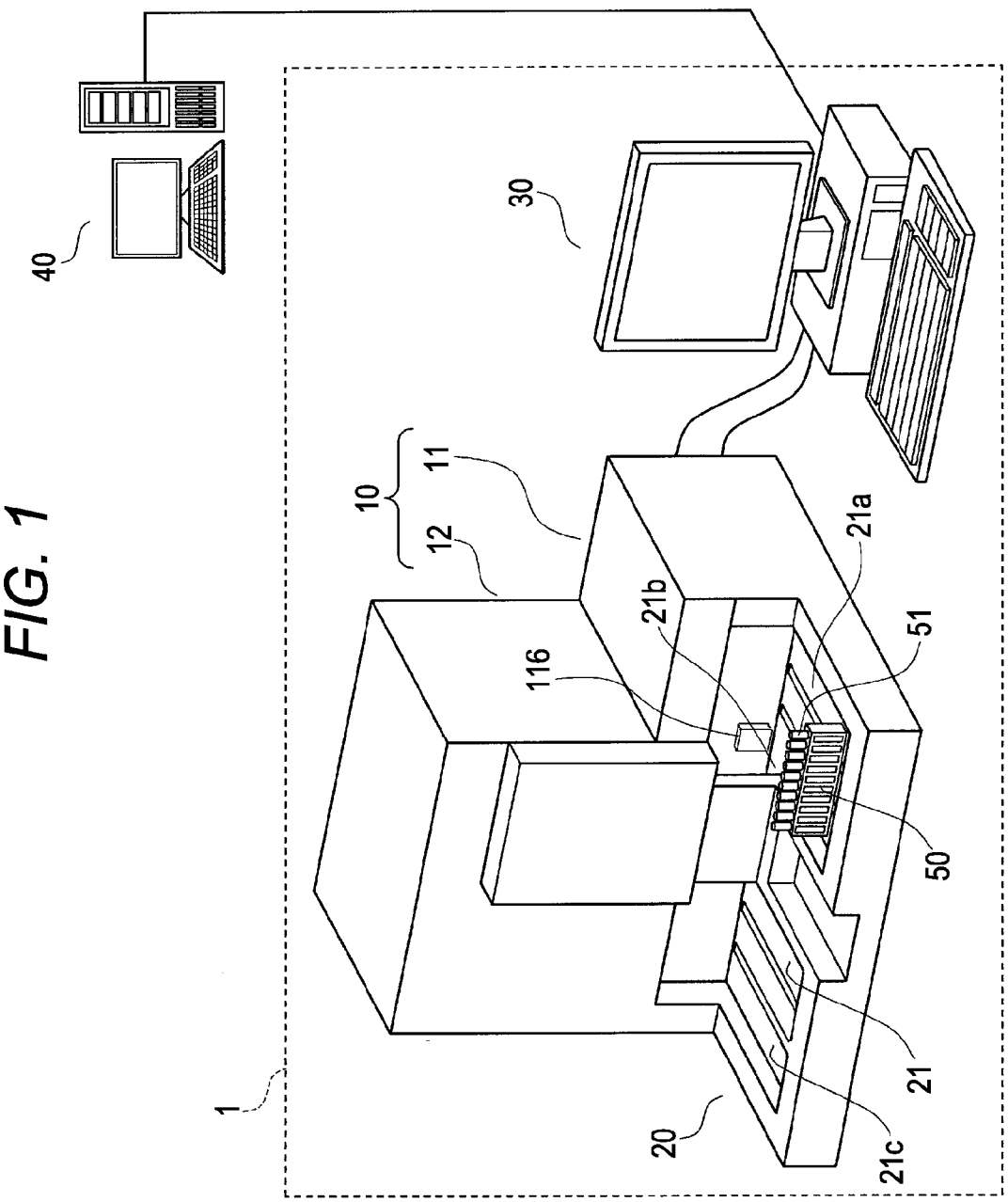
FIG. 1 is a view showing a configuration of an entire system including a urine sample testing apparatus according to an embodiment.

FIG. 1 is a view showing a configuration of an entire system including a urine sample testing apparatus 1. The urine sample testing apparatus 1 according to the present embodiment includes a measurement unit 10, a transport unit 20, and an information processing unit 30.

The measurement unit 10 includes a urine qualitative measuring section 11 for carrying out the urine qualitative test, and a urine sediment measuring section 12 for carrying out the urine sediment test. The urine qualitative measuring section 11 and the urine sediment measuring section 12 are communicably connected to each other. The urine qualitative measuring section 11 and the urine sediment measuring section 12 are respectively communicably connected to the information processing unit 30. The urine qualitative measuring section 11 is also communicably connected to the transport unit 20.

The transport unit 20 is a single unit common to the urine qualitative measuring section 11 and the urine sediment measuring section 12. The transport unit 20 is attached to the front surface of the measurement unit 10, and includes a transport path 21. The transport path 21 has a flat-plate shaped bottom surface one stage lower than the upper surface of the transport unit 20. A sample rack 50 transported on the transport path 21 is formed with ten holders to hold ten sample containers 51. The sample container 51 is transported on the transport path 21 with the sample rack 50 by being held in the holder of the sample rack 50. A barcode label (not shown) for specifying the sample is attached to the side surface of the sample container 51. The information processing unit 30 is communicably connected to a host computer 40 through a communication line.

The transport path 21 is configured by a square right tank region 21a arranged on the right side, a square left tank region 21c arranged on the left side, and a coupling region 21b for coupling the right tank region 21a and the left tank region 21c. When the sample rack 50 is mounted on the near side of the right tank region 21a by the user, the sample rack 50 mounted on the right tank region 21a is transferred backward (direction of approaching the measurement unit 10) and is positioned at the end on the far side of the right tank region 21a. The sample rack 50 positioned at the far side of the right tank region 21a is transferred leftward through the coupling region 21b.

The barcode reader 116 reads the barcode information from the barcode label attached to the sample container 51 positioned in front of the barcode reader 116. The barcode reader 116 is controlled by the control unit 111 of the urine qualitative measuring section 11, to be described later.

The coupling region 21b includes two aspirating positions for aspirating the sample from the sample container 51 held in the sample rack 50, where the sample is aspirated by the nozzle arranged in the urine qualitative measuring section 11 from the sample container 51 positioned at one aspirating position, and the sample is aspirated by the nozzle arranged in the urine sediment measuring section 12 from the sample container 51 positioned at the other aspirating position. The sample rack 50 in which the aspiration of all the samples is completed is transferred towards the left along the coupling region 21b, and positioned on the far side of the left tank region 21c.

The sample rack 50 positioned on the far side of the left tank region 21c is transferred frontward, and sequentially positioned on the near side of the left tank region 21c. The sample rack 50 positioned in front of the left tank region 21c is then taken out by the user.

Figure 2:
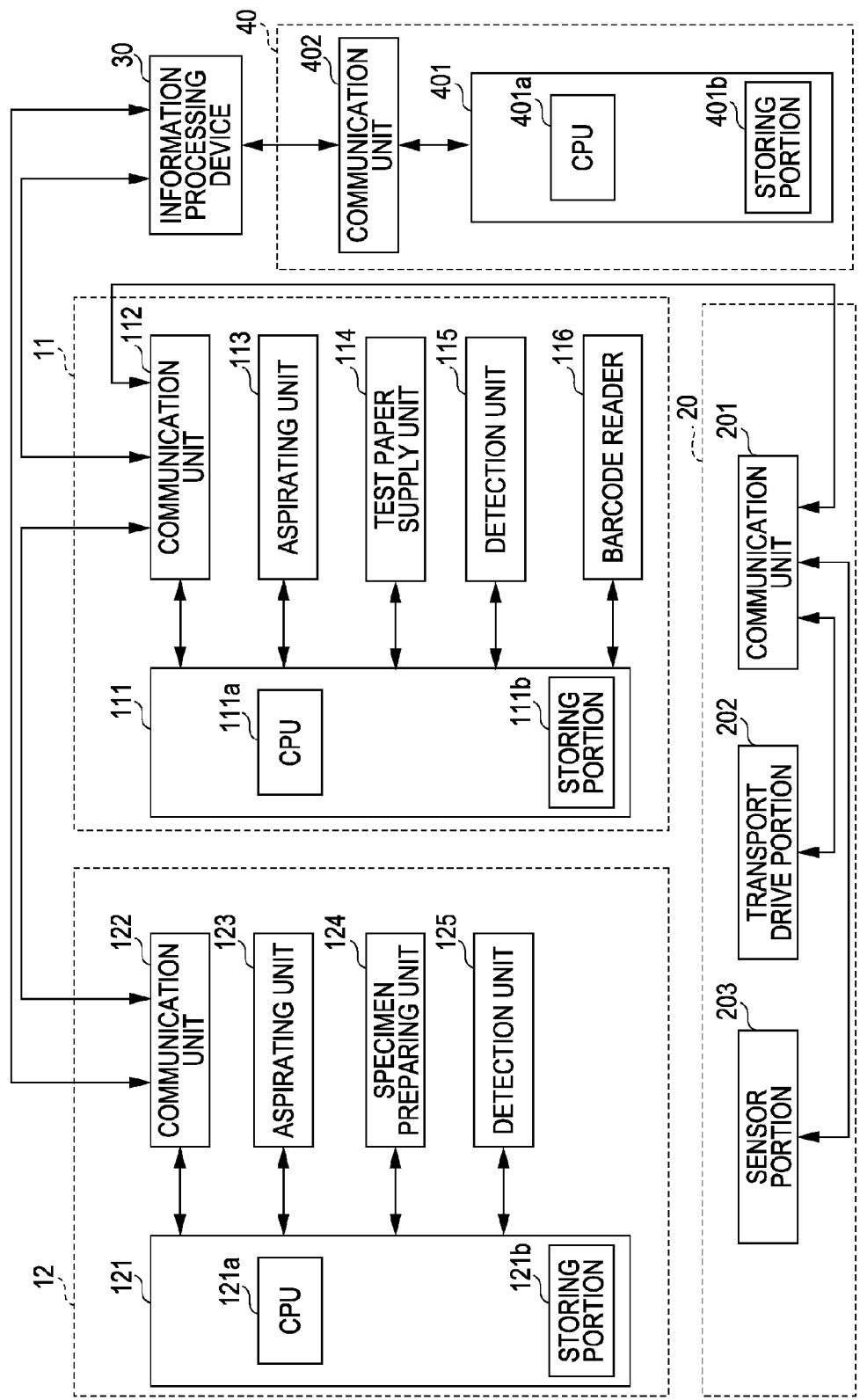
FIG. 2 is a view showing a circuit configuration of a urine qualitative measuring section, a urine sediment measuring section, a transport unit, and a host computer.

FIG. 2 is a view showing a circuit configuration of the urine qualitative measuring section 11, the urine sediment measuring section 12, the transport unit 20, and the host computer 40.

The urine qualitative measuring section 11 includes a control unit 111, a communication unit 112, an aspirating unit 113, a test paper supply unit 114, a detection unit 115, and a barcode reader 116. The control unit 111 includes a CPU 111a and a storing portion 111b. The CPU 111a executes the computer program stored in the storing portion 111b, and controls each unit of the urine qualitative measuring section 11. The CPU 111a controls each portion of the transport unit 20 through the communication unit 112. The storing portion 111b includes a storage means such as a ROM, a RAM, or a hard disc. The relevant urine qualitative measuring section 11 can carry out the measurement of the sample for a plurality of measurement items (urine qualitative measurement item). The urine qualitative measurement item includes glucose (GLU), protein (PRO), albumin (ALB), bilirubin (BIL), urobilinogen (URO), pH (PH), occult blood (BLD), ketone body (KET), nitrite salt (NIT), white blood cells (LEU), creatinine (CRE), and albumin/creatinine ratio (A/C).

The communication unit 112 processes the signal received from the control unit 111 and outputs the processed signal to the urine sediment measuring section 12, the transport unit 20, and the information processing unit 30, and processes the signal received from the urine sediment measuring section 12, the transport unit 20, and the information processing unit 30 and outputs the processed signal to the control unit 111. The aspirating unit 113 aspirates the sample in the sample container 51 positioned at one aspirating position through the nozzle of the urine qualitative measuring section 11. The test paper supply unit 114 retrieves the test paper necessary for the measurement from the test paper feeder containing the test paper, and spot attaches the sample aspirated by the aspirating unit 113 on the retrieved test paper. The detection unit 115 measures the test paper spot attached with the sample. The measurement data obtained by such measurement is output to the control unit 111, and analyzed by the control unit 111. The barcode reader 116 reads the barcode information from the barcode label attached to the sample container 51, and outputs the barcode information to the control unit 111.

The urine sediment measuring section 12 includes a control unit 121, a communication unit 122, an aspirating unit 123, a specimen preparing unit 124, and a detection unit 125. The control unit 121 includes a CPU 121a and a storing portion 121b. The CPU 121a executes the computer program stored in the storing portion 121b, and controls each unit of the urine sediment measuring section 12. The storing portion 121b includes a storage means such as a ROM, a RAM, or a hard disc. The urine sediment measuring section 12 can carry out the measurement of the sample for a plurality of measurement items (urine sediment measurement item). The urine sediment measurement item includes red blood cell (RBC), white blood cell (WBC), epidermal cell (EC), cast (CAST), bacteria (BACT), crystal (X'TAL), yeast like fungus (YLC), small round cell (SRC), pathological cast (Path. CAST) including cell component, mucus (MUCUS), sperm (SPERM), urine conductivity (Cond.), red blood cell morphology information (RBC-Info.), urine concentration information (Cond.-Info.), and UTI (urinary tract infection) information (UTI-Info.)

The communication unit 122 processes the signal received from the control unit 121 and outputs the processed signal to the urine qualitative measuring section 11 and the information processing unit 30, and processes the signal received from the urine qualitative measuring section 11 and the information processing unit 30 and outputs the processed signal to the control unit 111. The aspirating unit 123 aspirates the sample in the sample container 51 positioned at the other aspirating position described above through the nozzle of the urine sediment measuring section 12. The specimen preparing unit 124 mixes and stirs the sample aspirated by the aspirating unit 123 and the reagent necessary for the measurement, and prepares the specimen for measurement by the detection unit 125. The detection unit 125 measures the sample prepared by the specimen preparing unit 124. The measurement data obtained by such measurement is transmitted to the information processing unit 30.

The transport unit 20 includes a communication section 201, a transport drive section 202, and a sensor section 203. The communication section 201 processes the signal received from the urine qualitative measuring section 11 and outputs the processed signal to each section of the transport unit 20, and processes the signal received from each section of the transport unit 20 and outputs the processed signal to the urine qualitative measuring section 11.

The transport drive section 202 is controlled by the CPU 111a of the urine qualitative measuring section 11. The sensor section 203 includes various types of sensors arranged in the transport unit 20, and outputs the output signals from such sensors to the urine qualitative measuring section 11 through the communication section 201.

The host computer 40 includes a control unit 401 and a communication unit 402. The control unit 401 includes a CPU 401a and a storing portion 401b. The CPU 401a executes the computer program stored in the storing portion 401b, and returns the measurement order stored in the storing portion 401b when receiving an inquiry of the measurement order from the information processing unit 30. The CPU 401a also determines the measurement order of the urine sediment measuring section 12 based on the measurement data received from the urine qualitative measuring section 11 through the information processing unit 30 and the reference of measurement necessity stored in the storing portion 401b. The storing portion 401b includes a storage means such as a ROM, a RAM, or a hard disc.

Figure 3:
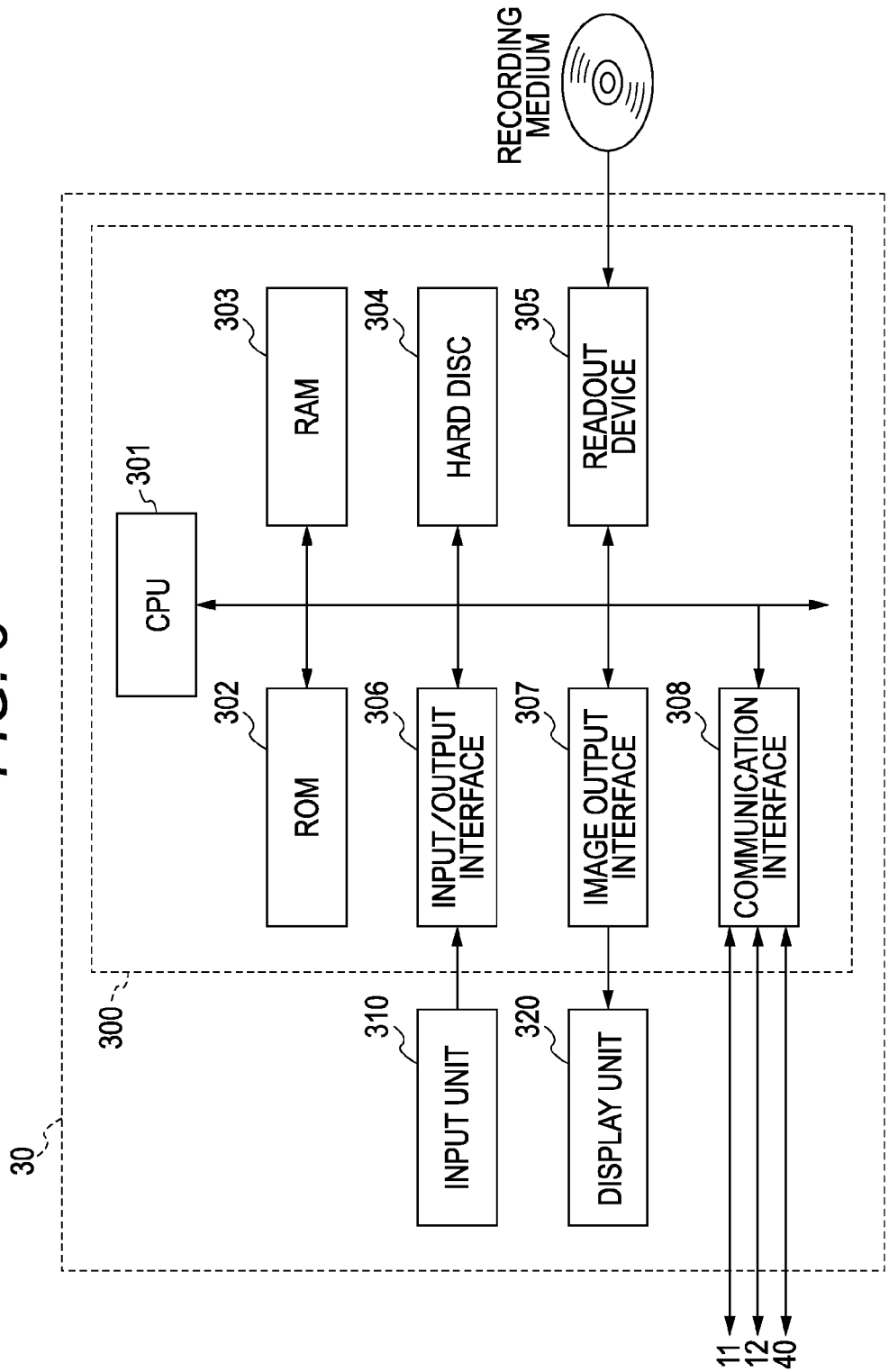
FIG. 3 is a block diagram showing a configuration of an information processing unit according to the embodiment.

FIG. 3 is a view showing a circuit configuration of the information processing unit 30.

The information processing unit 30 is configured by a personal computer and includes a main body 300, an input unit 310 and a display unit 320. The main body 300 includes a CPU 301, a ROM 302, a RAM 303, a hard disc 304, a read-out device 305, an input/output interface 306, an image output interface 307, and a communication interface 308.

The CPU 301 executes computer programs stored in the ROM 302 and the computer programs loaded in the RAM 303. The RAM 303 is used to read out the computer programs recorded on the ROM 302 and the hard disc 304. The RAM 303 is also used as a work region of the CPU 301 when executing the computer programs.

The hard disc 304 is installed with various computer programs to be executed by the CPU 301 such as operating systems and application programs and data used for the execution of the computer programs. In other words, the hard disc 304 is installed with a program for making an inquiry of the measurement order to the host computer 40 based on the inquiry of the measurement order, to be described later, transmitted from the urine qualitative measuring section 11 and the urine sediment measuring section 12, a program for transmitting the measurement order transmitted from the host computer 40 to the urine qualitative measuring section 11 and the urine sediment measuring section 12, and the like. The hard disc 304 is also installed with a program for carrying out display of the urine qualitative test result on the display unit 320 based on the measurement data transmitted from the urine qualitative measuring section 11, a program for carrying out display of the urine sediment test result on the display unit 320 based on the measurement data transmitted from the urine sediment measuring section 12, and the like.

The hard disc 304 includes a cross check set value database. FIG. 4 is a schematic view showing a configuration of the cross check set value database. The cross check set value database DB includes a table T1 for storing the set value of the combination (cross check target item) of the urine qualitative measurement item and the urine sediment measurement item, and a table T2 for storing cross check table information in each cross check target item.

The table T1 includes a field F11 for storing a set value number, a field F12 for storing a set value (use flag) on whether or not to use the record thereof, a field F13 for storing a set value (display flag) on whether or not to display the cross check mark in the measurement result screen, to be described later, a field F14 for storing the urine qualitative measurement item set as the cross check target item, and a field F15 for storing the urine sediment measurement item set as the cross check target item. In other words, each record of the table T1 includes a pair of urine qualitative measurement item and urine sediment measurement item specified as cross check target items, a use flag, and a display flag.

The table T2 includes a field F21 for storing the cross check target item set in the table T1, and a field F22 for storing the cross check table information corresponding to such cross check target item. The cross check table information is information used to determine whether or not the measurement value of the urine qualitative measurement item and the measurement value of the urine sediment measurement item, which are corresponding cross check target items, have specific relationship. The cross check table information will be described later.

Figure 5:
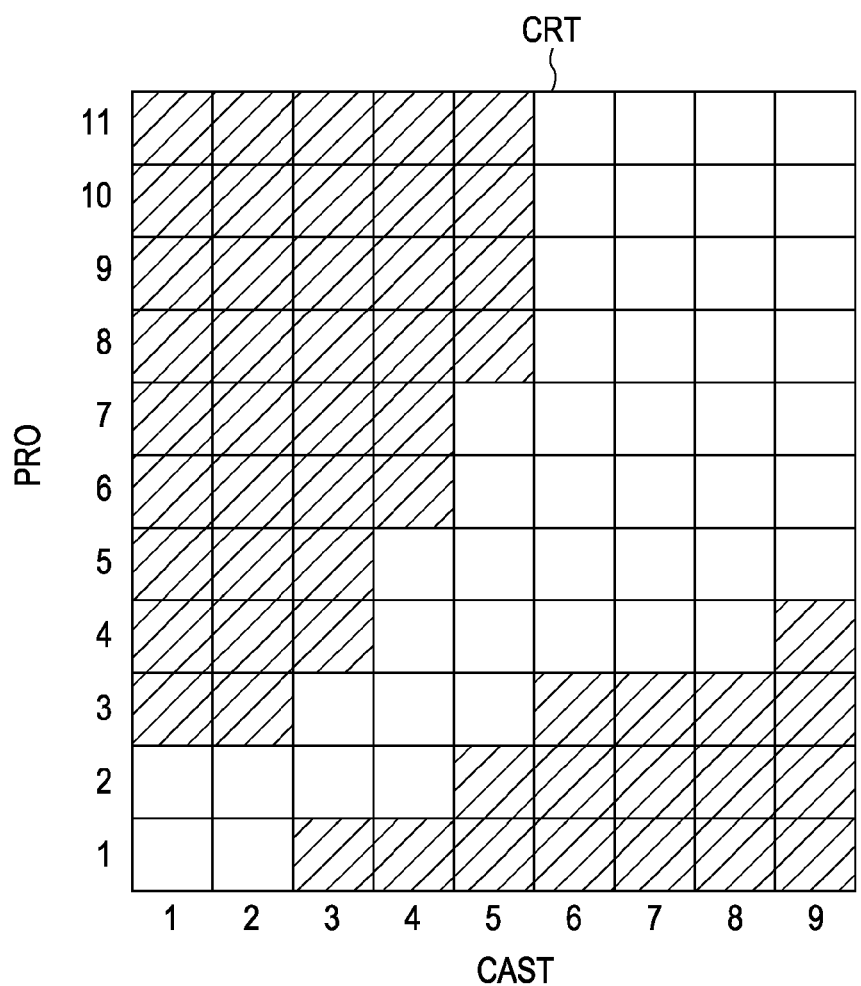
FIG. 5 is a view showing one example of a cross check table.

The information processing unit 30 according to the present embodiment can execute the cross check of the measurement result for determining whether or not the measurement result of the urine qualitative measuring section 11 and the measurement result of the urine sediment measuring section 12 have a predetermined relationship using the relevant cross check set value database DB. Specifically, if the combination of protein and cast is set in the cross check set value database DB as the cross check target item, whether or not the measurement result of the protein (PRO) by the urine qualitative measuring section 11 and the measurement result of the cast (CAST) by the urine sediment measuring section 12 of the same sample are in a relationship defined in the cross check table information of the table T2 is determined. FIG. 5 is a view showing one example of a cross check table. In the cross check table CRT shown in FIG. 5, the vertical axis shows the rank of the measurement value of the urine qualitative measurement item (protein) and the horizontal axis shows the rank of the measurement value of the urine sediment measurement item (cast). The rank is given by the rank set value stored in the hard disc 304. The rank set value will be described later. In the cross check table CRT, whether conformance (cell drawn with diagonal lines in the figure) or non-conformance (white cell in the figure) is set for each combination of the rank of the measurement value of the urine qualitative measurement item and the rank of the measurement value of the urine sediment measurement item. In the cross check of the measurement result, if the measurement value of the urine qualitative measurement item and the measurement value of the urine qualitative measurement item correspond to "conformance" in the cross check table CRT, such measurement values are determined to correspond to a predetermined relationship (e.g., reliability of measurement result is low), and if the measurement value of the urine qualitative measurement item and the measurement value of the urine qualitative measurement item correspond to "non-conformance", such measurement values are determined not to correspond to a predetermined relationship (e.g., reliability of measurement result is low). The cross check table information of the table T2 shows the cross check table CRT described above. Specifically, the cross check table information stored in the field F22 of the table T2 is expressed with the combination of two numerical values of "0" and "1", as shown in FIG. 4. Here, "0" indicates "non-conformance" in one cell of the cross check table CRT and "1" indicates "conformance". The data in which "0" and "1" respectively indicating "conformance" and "non-conformance" of each cell are lined in a predetermined order complying with the lining of each cell in the cross check table CRT is the cross check table information.

The readout device 305 is configured by a CD-ROM drive or DVD-drive and is capable of reading out a computer program and data recorded in a recording medium. The input unit 310 including mouse and keyboard is connected to the input/output interface 306, so that the user can use the input unit 310 to input data to the information processing unit 30. The image output interface 307 is connected to the display unit 320 configured by display, or the like, and outputs a video signal corresponding to the image data to the display unit 320. The display unit 320 displays the image based on the input video signal. The data can be transmitted and received with respect to the urine qualitative measuring section 11, the urine sediment measuring section 12 and the host computer 40 by the communication interface 308.

[Operation of Urine Sample Testing Apparatus]
<Cross Check Setting Process>

The operation of the urine sample testing apparatus 1 according to the present embodiment will be described below. The cross check setting process of the urine sample testing apparatus 1 will be described first. The cross check setting process is a process of setting the combination of the urine qualitative measurement item and the urine sediment measurement item specified by the user as the target items of cross check, to be described later.

Figure 6:
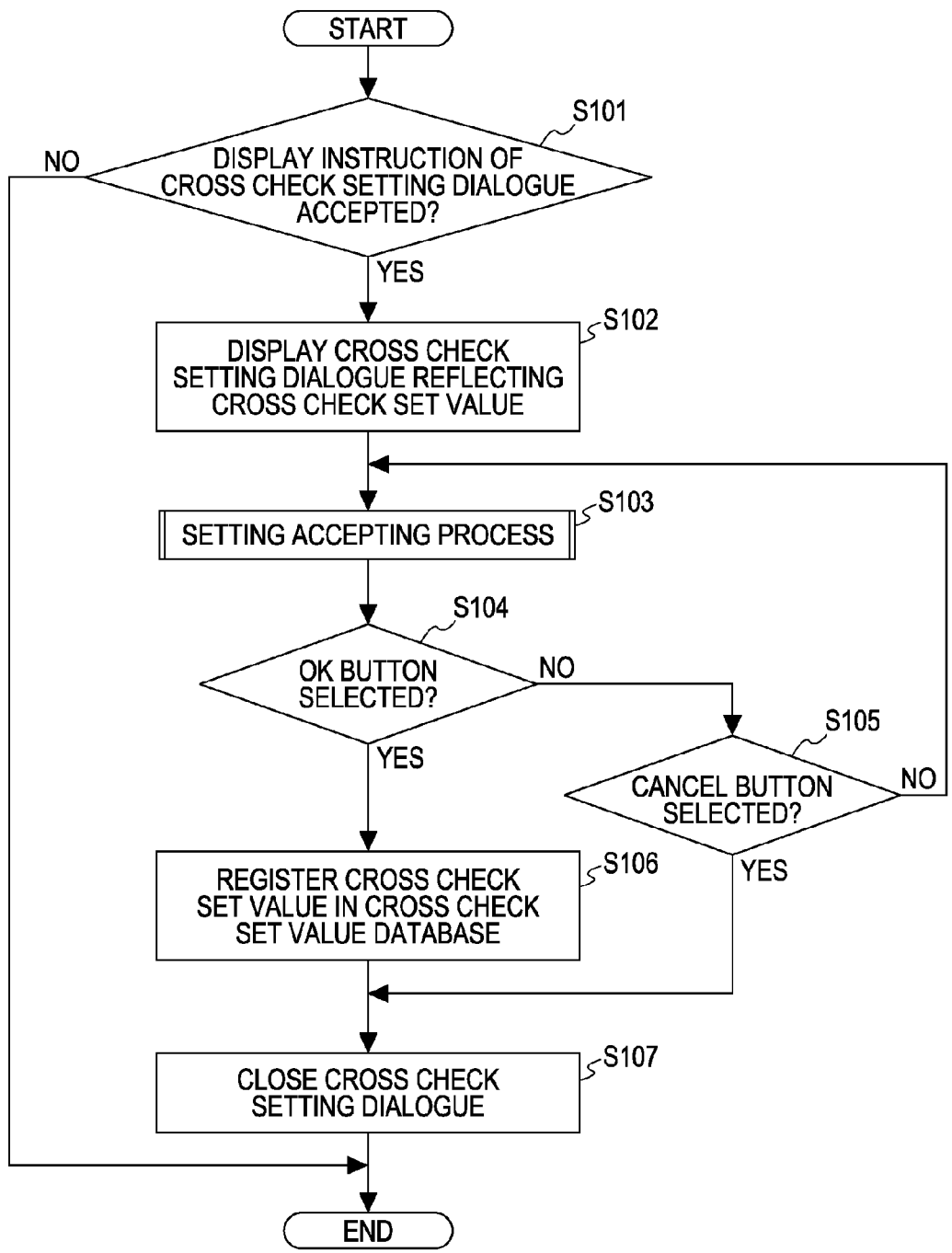
FIG. 6 is a flowchart showing the procedure of the cross check setting process in the urine sample testing apparatus according to the embodiment.

FIG. 6 is a flowchart showing the procedure of the cross check setting process in the urine sample testing apparatus 1 according to the present embodiment.

First, the CPU 301 of the information processing unit 30 determines whether or not a display instruction of the cross check setting dialogue is accepted from the user (step S101). The cross check setting dialogue is a screen for the user to specify the combination of the urine qualitative measurement item and the urine sediment measurement item as the target items of the cross check. If the display instruction of such cross check setting dialogue is not accepted (NO in step S101), the CPU 301 terminates the process.

If the display instruction of the cross check setting dialogue is accepted (YES in step S101), the CPU 301 reads out the cross check set value from the hard disc 304, displays the cross check setting dialogue reflecting the cross check set value on the display unit 320 (step S102), and executes a setting accepting process (step S103).

Figure 7:
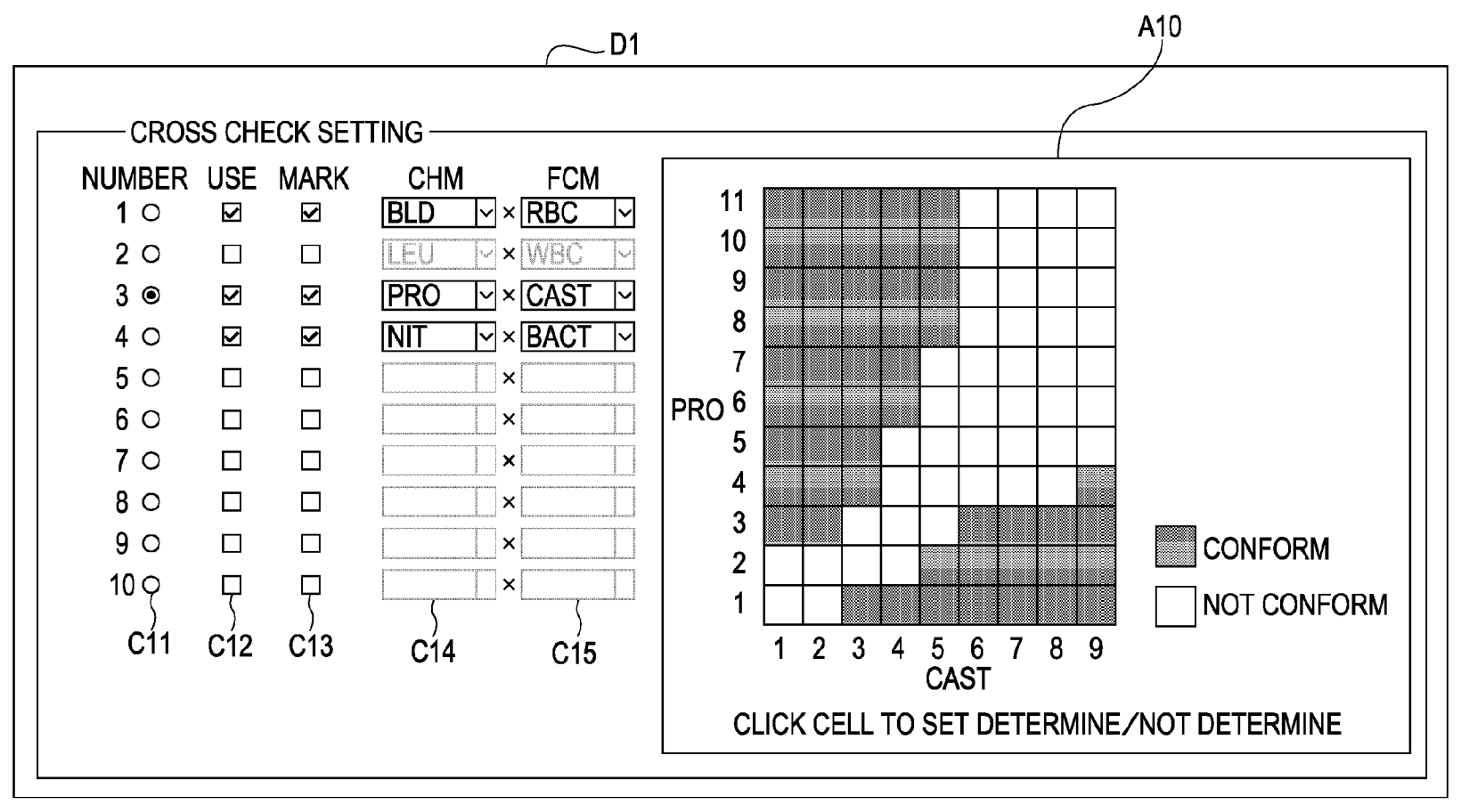

FIG. 7 is a view showing one example of the cross check setting dialogue. As shown in the figure, in the cross check setting dialogue D1, up to ten cross check set values can be registered. In the cross check setting dialogue D1, the number (1 to 10) of the cross check set value is vertically lined for display, and a radio button C11 is displayed next to each number. The check box 12 for specifying whether or not to use such cross check set value is arranged on the right of each radio button C11. A check box C13 for specifying whether or not to display the cross check mark in the measurement result screen, to be described later, is arranged on the right side of each check box C12. Furthermore, selection boxes C14, C15 for specifying the cross check target item are arranged on the right side of each check box C13.

Figure 8:
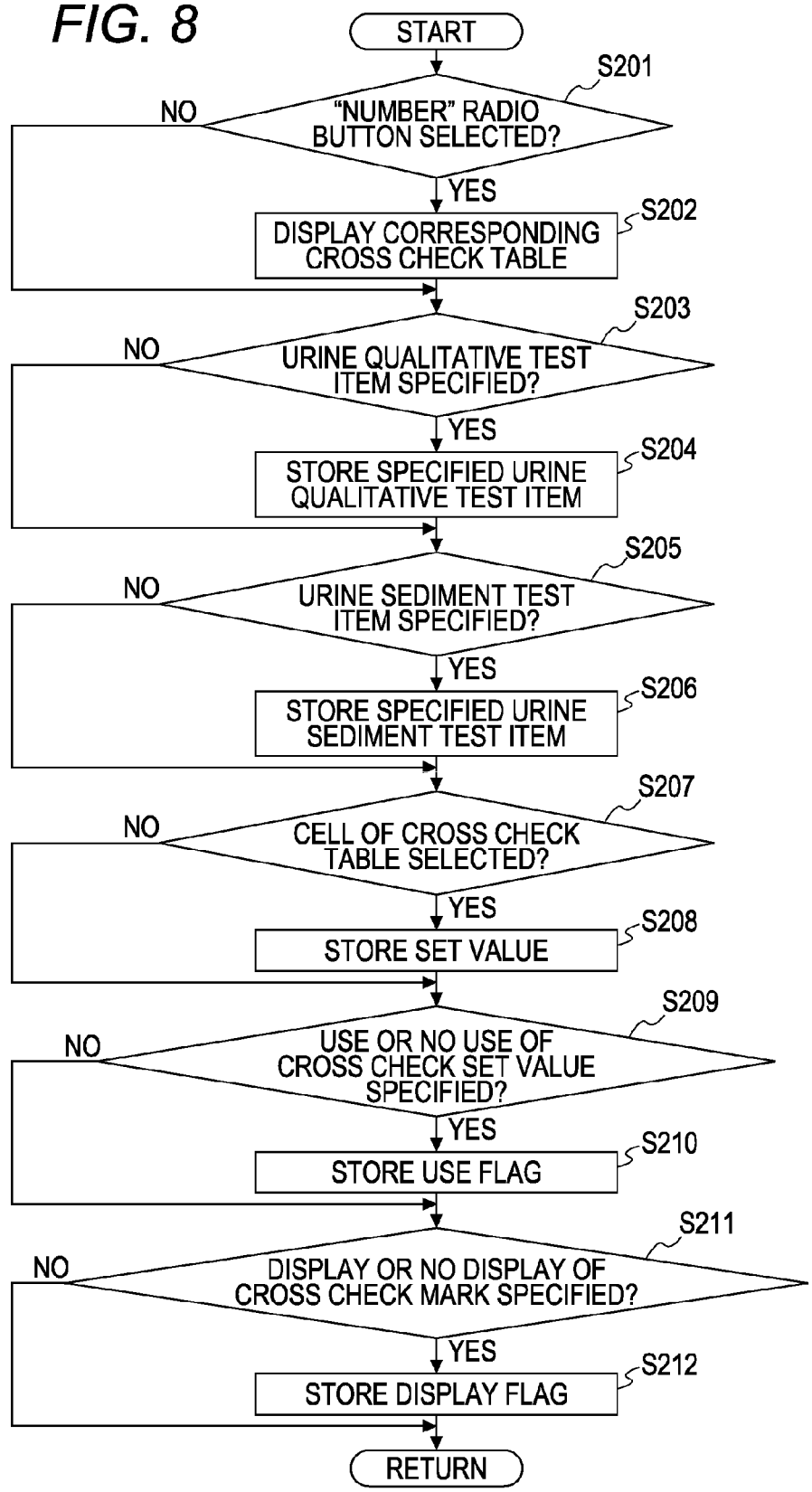
FIG. 8 is a flowchart showing the procedure of the setting accepting process.

FIG. 8 is a flowchart showing the procedure of the setting accepting process. In the setting accepting process, the CPU 301 first determines whether or not one of the radio buttons C11 is selected (step S201). In the cross check setting dialogue D1, the user selects one of the ten radio buttons C11 by operating the input unit 310. If the selection of one of the radio buttons C11 is accepted (YES in step S201), the CPU 301 displays the cross check table of the cross check target item corresponding to the radio button C11 in the region A10 on the right side of the cross check setting dialogue D1 (step S202), and proceeds the process to step S203. If the cross check target item corresponding to the selected radio button C11 is not specified with the selection boxes C14, C15, the cross check table is not displayed until the cross check target item, to be described later, is specified. If the selection of the radio button C11 is not accepted in step S201 (NO in step S201), the CPU 301 proceeds the process to step S203.

In step S203, the CPU 301 determines whether or not the specification of the urine qualitative measurement item is accepted as the cross check target item by one of the selection boxes C14 (step S203). When the downward arrow symbol on the right side of the selection box C14 is selected, the pull down menu of the list of all urine qualitative measurement items is displayed, so that the user can specify one urine qualitative measurement item from the list. If the specification of the urine qualitative measurement item is accepted in step S203 (YES in step S203), the CPU 301 stores the specified urine qualitative measurement item in the RAM 303 in correspondence with the set value number (step S204), and proceeds the process to step S205. If the specification of the urine qualitative measurement item is not accepted in step S203 (NO in step S203), the CPU 301 proceeds the process to step S205.

In step S205, the CPU 301 determines whether or not the specification of the urine sediment measurement item is accepted as the cross check target item by one of the selection boxes C15 (step S205). When the downward arrow symbol on the right side of the selection box C15 is selected, the pull down menu of the list of all urine sediment measurement items is displayed, so that the user can specify one urine sediment measurement item from the list. If the specification of the urine sediment measurement item is accepted in step S205 (YES in step S205), the CPU 301 stores the specified urine sediment measurement item in the RAM 303 in correspondence with the set value number (step S206), and proceeds the process to step S207. If the specification of the urine sediment measurement item is not accepted in step S205 (NO in step S205), the CPU 301 proceeds the process to step S207.

In step S207, the CPU 301 determines whether or not the selection of the cell of the cross check table displayed in the region A10 is accepted (step S207). Each cell of the cross check table displayed in the region A10 indicates whether or not the rank of the measurement value of the urine qualitative measurement item and the rank of the measurement value of the urine sediment measurement item corresponding to the relevant cell conform with a predetermined relationship. In other words, the blue (indicated with diagonal lines in the figure) cell indicates conformance to the predetermined relationship, and the white cell indicates non-conformance to the predetermined relationship. Each cell of the relevant cross check table is selectable. When the user selects one cell of the cross check table by operating the input unit 310, the cell is changed to white if blue, or the cell is changed to blue if white. That is, the cell is changed to a cell that is non-conformance to the predetermined relationship when the cell conforming to the predetermined relationship is selected, and the cell is changed to the cell conforming to the predetermined relationship when the cell non-conforming to the predetermined relationship is selected.

If the selection of the cell of the cross check table is accepted in step 207 (YES in step S207), the CPU 301 stores the specified set value in the RAM 303 in correspondence with the set value number (step S208), and proceeds the process to step S209. If the selection of the cell of the cross check table is not accepted in step S207 (NO in step S207), the CPU 301 proceeds the process to step S209.

In step S209, the CPU 301 determines whether or not the specification to use or not use the cross check set value is accepted by selecting one of the check boxes C12 (step S209). The cross check set value which check box C12 is selected (checked) is used in the cross check. The cross check set value which check box C12 is not selected (unchecked) is not used in the cross check. If the specification to use or not use the cross check set value is accepted in step S209 (YES in step S209), the CPU 301 stores the use flag of the cross check set value in the RAM 303 in correspondence with the set value number (step S210), and proceeds the process to step S211. "0" is stored in the use flag if specified not to use the cross check set value, and "1" is stored in the use flag if specified to use the cross check set value. If the specification to use or not use the cross check set value is not accepted in step S209 (NO in step S209), the CPU 301 proceeds the process to step S211.

In step S211, the CPU 301 determines whether or not the specification to display or not display the cross check mark is accepted by selecting one of the check boxes C13 (step S211). If the check box C13 is selected (checked), the cross check mark indicating conformance to the predetermined relationship is displayed in the measurement result screen described later to call the attention of the user when the measurement result of the sample conforms to the predetermined relationship defined in the cross check table. If the check box C13 is not selected (unchecked), the cross check mark is not displayed in the measurement result screen even if the measurement result of the sample conforms to the predetermined relationship. If the specification to display or not display the cross check mark is accepted in step S211 (YES in step S211), the CPU 301 stores the display flag of the cross check set value in the RAM 303 in correspondence with the set value number (step S212), and returns the process to the callout address of the setting accepting process in the main routine. If the specification to display or not display the cross check mark is not accepted in step S211 (NO in step S211), the CPU 301 returns the process to the callout address of the setting accepting process in the main routine.

Returning back to FIG. 6, the CPU 301 determines whether or not the OK button arranged in the cross check setting dialogue D1 is selected in step S104 (step S104). If the OK button is not selected (NO in step S104), the CPU 301 determines whether or not the cancel button arranged in the cross check setting dialogue D1 is selected (step S105). If the cancel button is not selected (NO in step S105), the CPU returns the process to step S103, and again executes the setting accepting process.

If the OK button is selected in step S104 (YES in step S104), the CPU 301 registers the cross check set value stored in the RAM 303 in the cross check set value database DB (step S106). That is, the CPU 301 registers the combination of the urine qualitative measurement item and a plurality of urine sediment measurement items specified by the user in the cross check set value database as the set value of the cross check target item. The CPU 301 then closes the cross check setting dialogue (step S107), and terminates the process. If the cancel button is selected in step S105 (YES in step S105), the CPU 301 discards the cross check set value stored in the RAM 303, closes the cross check setting dialogue (step S107), and terminates the process.

In the information processing unit 30, the rank value described above can be set for the urine sediment measurement item. A rank value setting dialogue is displayed on the display unit 320 when the user makes a predetermined input through the input unit 310. FIG. 9 is a view showing one example of the rank value setting dialogue. The user can set the rank value using the rank value setting dialogue.

The rank value can be set only for the urine sediment measurement item. The rank value for the urine qualitative measurement item is given in advance, and the user cannot change the setting. As shown in FIG. 9, the rank value setting dialogue D2 includes a selection box C21 for specifying the urine sediment measurement item. When the selection box C21 is selected, the pull down menu of the list of all urine sediment measurement items is displayed, so that the user can specify one urine sediment measurement item from the list.

The rank values of 1 to 9 are vertically lined for display at the lower side of the selection box C21, where an input box C22 for specifying the range of the measurement value corresponding to the respective rank value is arranged on the right side of the respective rank value. More specifically, an upper limit value of the measurement value corresponding to the rank value is input to the nine input boxes C22 corresponding to the rank values 1 to 9. For instance, the upper limit value of the measurement value corresponding to the rank value 1 of the urine sediment measurement item specified by the selection box C21 is input to the input box C21 of the rank value 1. In the example of FIG. 9, 6/µL is specified as the upper limit value of the measurement value corresponding to the rank value 1 for the measurement item "red blood cells".

The user specifies the urine sediment measurement item to be set with the rank value and the upper limit value of the measurement value corresponding to each rank value using the rank value setting dialogue D2. When the user selects the OK button arranged in the rank value setting dialogue D2 with the set value of the rank value input, the input rank set value is stored in the hard disc 304. When the cancel button arranged in the rank value setting dialogue D2 is selected, the input rank set value is discarded and the rank value setting dialogue is closed.

<Sample Analyzing Operation>

Figure 10A:
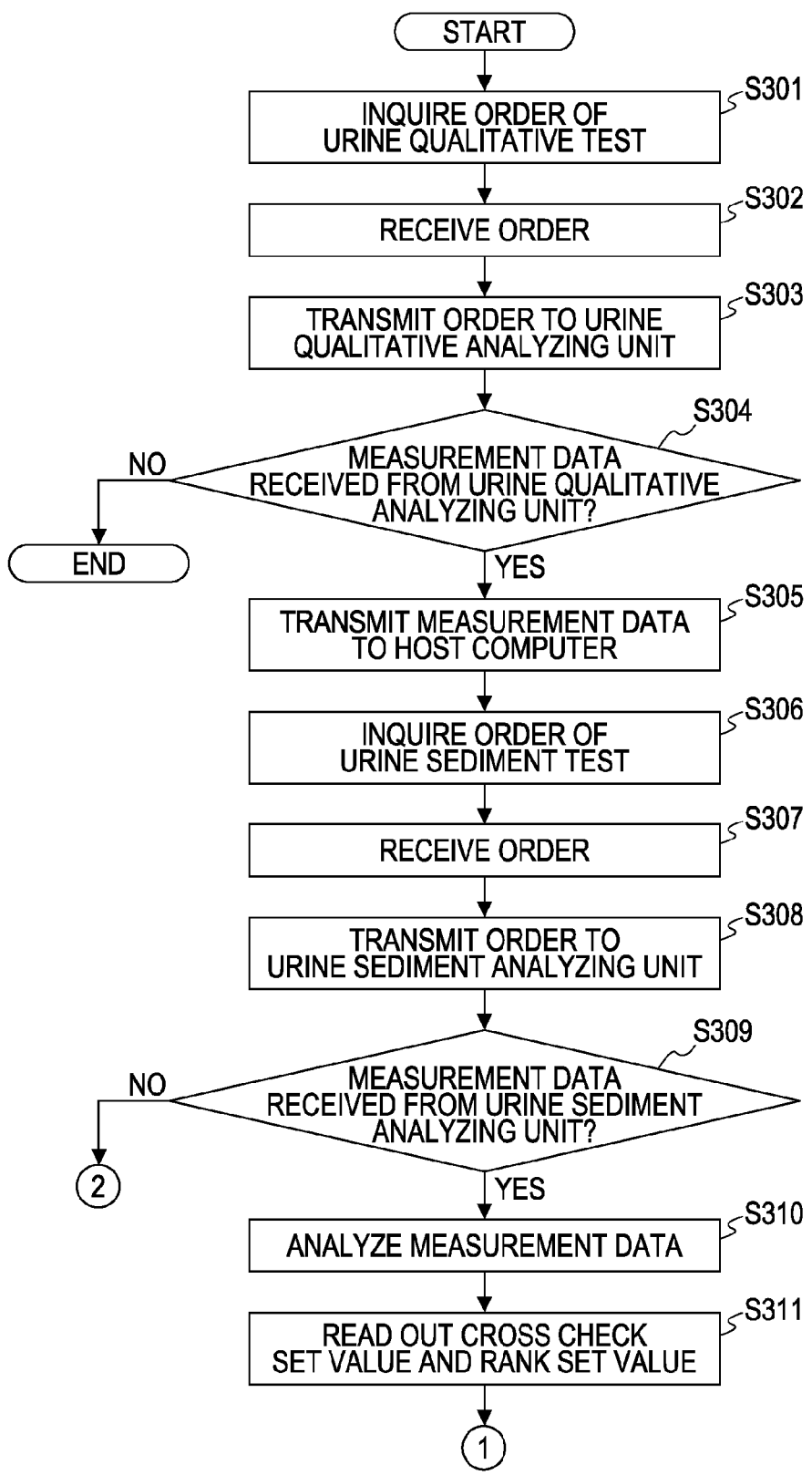
FIG. 10A and FIG. 10B are flowcharts showing the processing procedure by the information processing unit in the sample analyzing operation of the urine sample testing apparatus according to the embodiment.
Figure 10B:
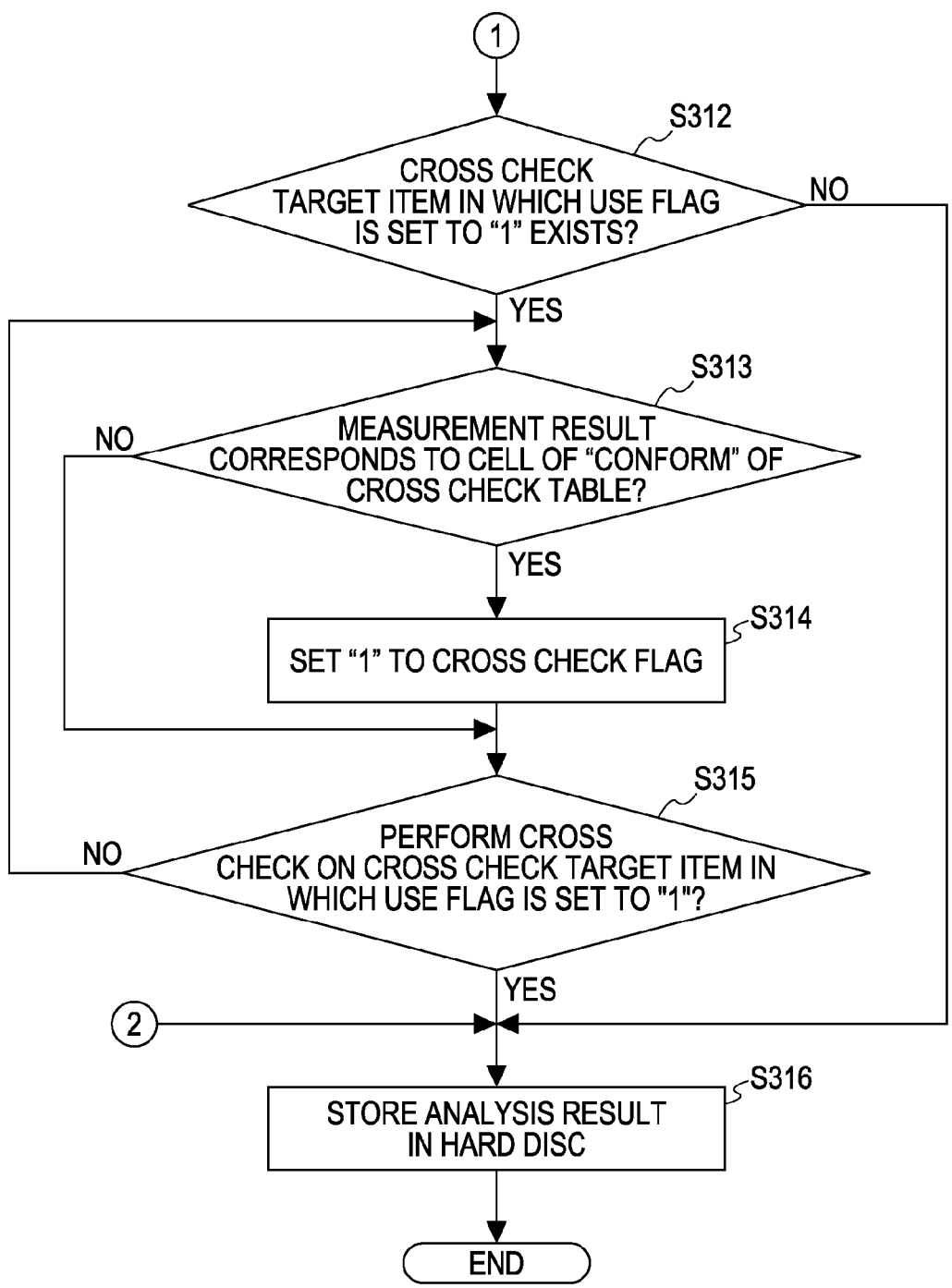

The sample analyzing operation by the urine sample testing apparatus 1 will now be described. FIG. 10A and FIG. 10B are flowcharts showing the processing procedure by the information processing unit 30 in the sample analyzing operation of the urine sample testing apparatus 1 according to the present embodiment. The sample analyzing operation starts when the user operates the input unit 310 of the information processing unit 30 to input an instruction to start the sample analysis to the urine sample testing apparatus 1. After the sample analyzing operation is started, the sample rack 50 is transported by the transport unit 20. The CPU 111a of the urine qualitative measuring section 11 reads out the barcode information from the barcode label attached to the sample container 51 transported by the transport unit 20 with the barcode reader 116, and inquires the information processing unit 30 regarding the measurement order of the urine qualitative measuring section 11 for the sample indicated by the barcode information.

The information processing unit 30 makes an inquiry on the measurement order of the urine qualitative test to the host computer 40 (step S301). The measurement order of the sample is registered in advance in the host computer 40, where the host computer 40 transmits the measurement order to the information processing unit 30 in response to the inquiry if the measurement order that matches the inquiry is in the registered measurement orders. When receiving the measurement order from the host computer (step S302), the information processing unit 30 transmits the measurement order to the urine qualitative measuring section 11 (step S303). Such measurement order includes the urine qualitative measurement item to be measured and the necessity of measurement. When the urine qualitative measuring section 11 receives the measurement order from the information processing unit 30, the CPU 111a determines whether or not the measurement is necessary in the urine qualitative measuring section 11 for the relevant sample.

When determining that the measurement needs to be carried out in the urine qualitative measuring section 11, the CPU 111a aspirates the sample from the sample container 51 with the nozzle of the urine qualitative measuring section 11 and carries out the measurement of the relevant sample in the urine qualitative measuring section 11. When determining that the measurement is not necessary in the urine qualitative measuring section 11, the CPU 111a does not carry out the measurement of such sample.

The CPU 301 determines whether or not the measurement data is received from the urine qualitative measuring section 11 (step S304). If the measurement data is not received from the urine qualitative measuring section 11 (NO in step S304), the CPU 301 terminates the process. If the measurement data is received from the urine qualitative measuring section 11 in step S304 (YES in step S304), the CPU 301 transmits the relevant measurement data (urine qualitative measurement result of sample) to the host computer 40 (step S305). When receiving the measurement data of the urine qualitative measuring section 11, the CPU 401a of the host computer 40 determines the measurement order of the urine sediment measuring section 12 based on the measurement data and the reference of measurement necessity stored in the storing portion 401b in advance.

When the sample container 51 is positioned at the sample aspirating position of the urine sediment measuring section 12, the CPU 121a of the urine sediment measuring section 12 inquires the information processing unit 30 regarding the measurement order of the urine sediment measuring section 12. Upon receiving such inquiry, the information processing unit 30 makes an inquiry on the measurement order of the urine sediment test to the host computer 40 (step S306). If the measurement order that matches the inquiry is in the measurement orders registered in the host computer 40, the host computer 40 transmits the measurement order to the information processing unit 30 in response to the inquiry. When receiving the measurement order from the host computer (step S307), the information processing unit 30 transmits the measurement order to the urine sediment measuring section 12 (step S308). Such measurement order includes the urine sediment measurement item to be measured and the necessity of measurement. When the urine sediment measuring section 12 receives the measurement order from the information processing unit 30, the CPU 121a determines whether or not measurement is necessary in the urine sediment measuring section 12 for the relevant sample.

When determining that the measurement needs to be carried out in the urine sediment measuring section 12, the CPU 121a aspirates the sample from the sample container 51 with the nozzle of the urine sediment measuring section 12, and carries out the measurement of the relevant sample in the urine sediment measuring section 12. The measurement data of the sample is provided from the urine sediment measuring section 12 to the information processing unit 30, and analyzed by the CPU 301 of the information processing unit 30. When determining that the measurement is not necessary in the urine sediment measuring section 12, the CPU 121a does not carry out the measurement of such sample.

The CPU 301 determines whether or not the measurement data is received from the urine sediment measuring section 12 (step S309). If the measurement data is not received from the urine sediment measuring section 12 (NO in step S309), the CPU 301 proceeds the process to step S316, stores only the result of the urine qualitative test in the hard disc 304 (step S316), and terminates the process. If the measurement data is received from the urine sediment measuring section 12 in step S309 (YES in step S309), the CPU 301 analyzes the measurement data to obtain the urine sediment measurement result of the sample (step S310).

The CPU 301 then reads out the cross check set value registered in the cross check set value database DB and the rank set value stored in the hard disc 304 (step S311), and determines whether or not the cross check target item in which the use flag is set to "1" exists in the read cross check set value (step S312). If the cross check target item in which the use flag is set to "1" does not exist in step S312 (NO in step S312), the process proceeds to step S316 to store the urine qualitative test result and the urine sediment test result in the hard disc 304 (step S316) and terminates the process.

If the cross check target item in which the use flag is set to "1" exists in step S312 (YES in step S312), the CPU 301 determines whether or not the measurement result of the sample for the urine qualitative measurement item set as the cross check target item in which the use flag is set to "1" and the measurement result of the sample for the urine sediment measurement item set as the cross check target item corresponding to the urine qualitative measurement item correspond to the cell of "conformance" in the cross check table (step S313).

If the urine qualitative measurement result and the urine sediment measurement result correspond to "conformance" in the cross check table in step S313 (YES in step S313), the CPU 301 sets "1" (value indicating that urine qualitative measurement result and urine sediment measurement result correspond to "conformance" in cross check table) to the information (hereinafter referred to as "cross check flag") indicating whether or not the urine qualitative measurement result and the urine sediment measurement result correspond to "conformance" in the cross check table in correspondence with the cross check target item and stores the cross check flag in the RAM 303 (step S314), and proceeds the process to step S315. Furthermore, the initial value of the cross check flag is set to "0" (value indicating the urine qualitative measurement result and urine sediment measurement result correspond to "non-conformance" in the cross check table), and stored in the RAM 303. If the urine qualitative measurement result and the urine sediment measurement result do not correspond to "conformance" in the cross check table in step S313 (NO in step S313), the CPU 301 proceeds the process to step S315.

In step S315, the CPU 301 determines whether or not the cross check of the measurement result is carried out for all the cross check target items in which the user flag is set to "1" (step S315), and returns the process to step S313 if there is still the cross check target item in which the cross check is not yet carried out (NO in step S315), and executes the cross check of the measurement result for the cross check target item in which the use flag is set to "1" and the cross check is not yet carried out (step S313). If the cross check of the measurement result is completed for all the cross check target items in which the use flag is set to "1" (YES in step S315), the CPU 301 stores the analysis result (including cross check flag) in the hard disc 304 (step S316), and terminates the process.

<Measurement Result Display Operation>

The measurement result display operation of the urine sample testing apparatus 1 according to the present embodiment will now be described. In the urine sample testing apparatus 1 according to the present embodiment, the measurement result display operation can be carried out by having the CPU 301 of the information processing unit 30 execute the measurement result display process described below.

Figure 11:
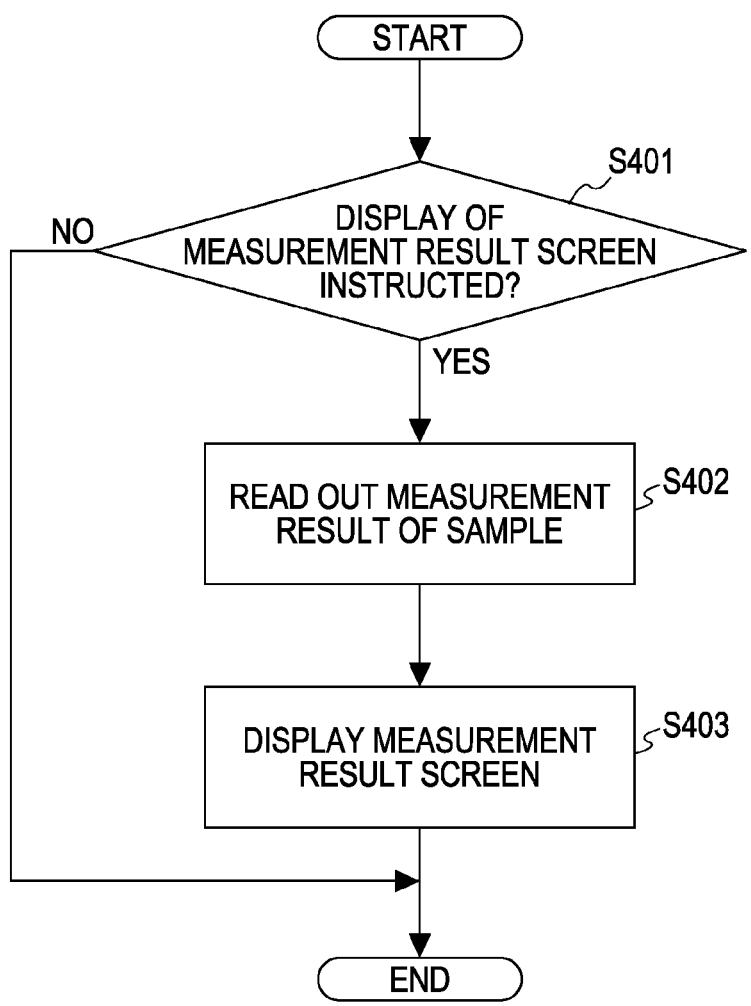
FIG. 11 is a flowchart showing the procedure of the measurement result display process in the information processing unit according to the embodiment.

FIG. 11 is a flowchart showing the procedure of the measurement result display process in the information processing unit 30 according to the present embodiment.

A measurement result screen is displayed on the display unit 320 when the user performs a predetermined input through the input unit 310. The CPU 301 determines whether or not the instruction to display the measurement result screen is accepted from the user (step S401). If the instruction to display the measurement result screen is not accepted (NO in step S401), the CPU 301 terminates the process. If the instruction to display the measurement result screen is accepted in step S401 (YES in step S401), the CPU 301 reads out the measurement result (analysis result stored in step S316) of the sample from the hard disc (step S402), displays the measurement result screen on the display unit 320 (step S403), and terminates the process.

Figure 12:
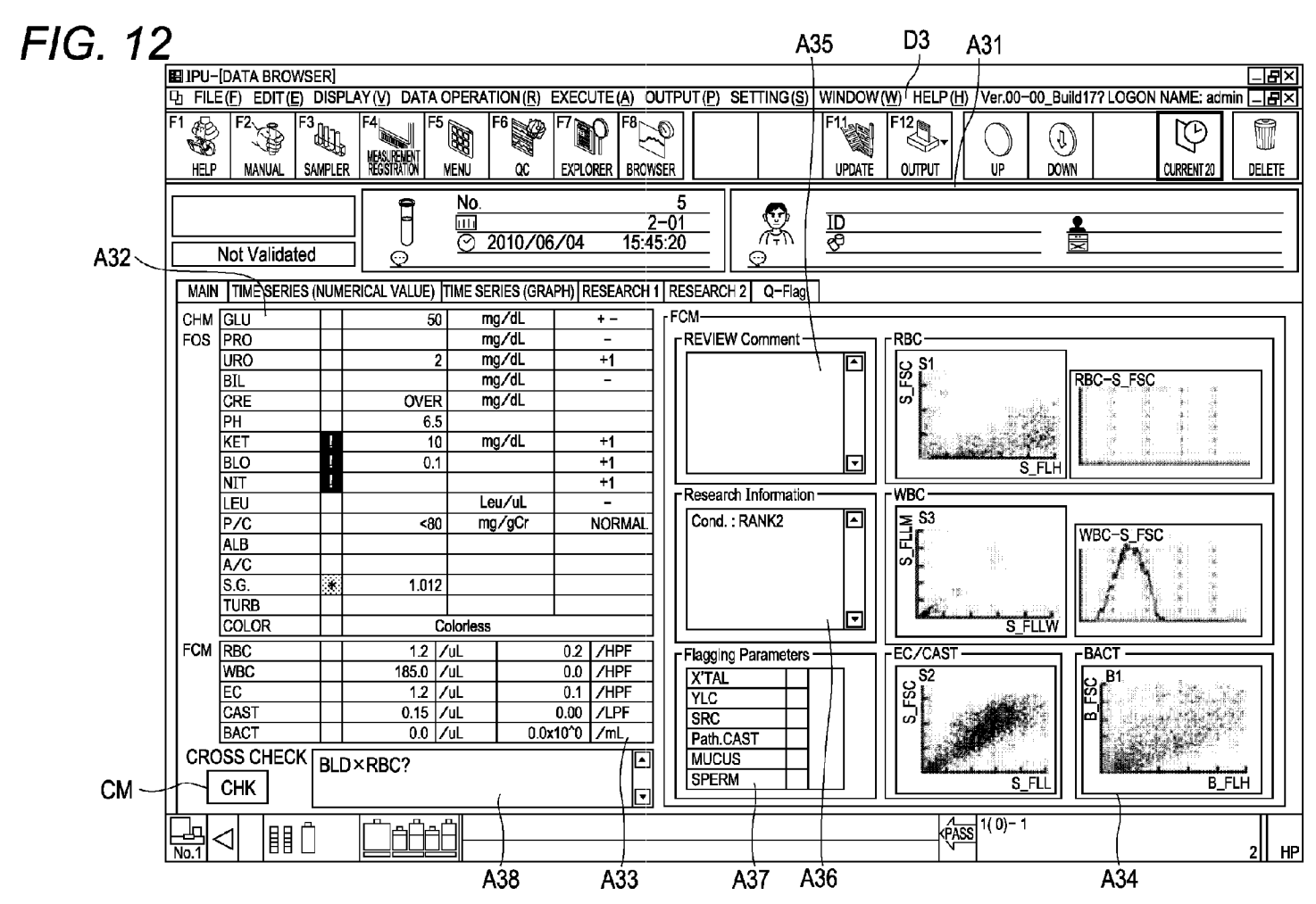

FIG. 12 is a view showing one example of a measurement result screen. The measurement result screen D3 includes a display region A31 of the sample information such as sample ID, patient name, test date etc., a display region A32 of the measurement value of the urine qualitative measurement item, a display region A33 of the measurement value (numerical data) of the urine sediment measurement item, and a display region A34 of a particle size distribution diagram (scattergram and histogram) contained in the urine sediment measurement result. The information related to the sample which measurement result is displayed in the measurement result screen is displayed in the display region A31. The measurement result obtained by the urine qualitative measuring section 11 for the relevant sample is displayed in the display region A32. The measurement result obtained by analyzing the measurement data obtained by the urine sediment measuring section 12 for the same sample by the information processing unit 30 is displayed in the display regions A32, A33.

The measurement result screen D3 also includes a display region A35 for displaying information (review comment) on abnormality when abnormality is detected in the measurement of the sample and determination is made that the retest is necessary for the relevant sample, a display region A36 for displaying the sample measurement result of the item set as the research item in advance of the urine sediment measurement item, and a display region A37 for displaying the sample measurement result of the item set as the flag item in advance of the urine sediment measurement item.

The measurement result screen D3 further includes a display region A38 for displaying the result of the cross check. In the relevant display region A38, when the cross check target item determined that the urine qualitative measurement result and the urine sediment measurement result correspond to a predetermined relationship in the cross check exists, such cross check target item name (information indicating combination of urine qualitative measurement item and urine sediment measurement item) is displayed. That is, the cross check target item name in which "1" is set to the cross check flag is displayed in the display region A38. In the illustrated example, the information "BLD×RBC?" indicating the combination of the occult blood (BLD) of the urine qualitative measurement item and the red blood cells (RBC) of the urine sediment measurement item is displayed in the display region A38, indicating that the determination is made that the measurement results corresponds to a predetermined relationship in the cross check target item of the combination of the occult blood (BLD) of the urine qualitative measurement item and the red blood cells (RBC) of the urine sediment measurement item.

Therefore, notification is made that the measurement result of the urine qualitative measurement item and the measurement result of the urine sediment measurement item of the cross check target item are in a predetermined relationship by displaying the cross check target item name in the display region A38. Therefore, if the predetermined relationship indicates that the reliability of the measurement result is low, the user can easily recognize that the reliability of the measurement result of the sample for the cross check target item is low by checking the display of the display region A38. If the predetermined relationship indicates that a predefined illness is suspected with respect to the patient, the user can easily recognize that such illness is being suspected by checking the display of the display region A38. In this case, the user can take necessary countermeasures such as checking the measurement results of other measurement items or conduct more specific tests of the sample.

If the measurement result includes the cross check target item in which "1" is set for the cross check flag, and "1" is set for the display flag of the cross check target item in the cross check set value database DB, a cross check marker CM for promoting the attention of the user is displayed next to the display region A38. The cross check mark CM is displayed with a color (yellow in the present embodiment) that calls the attention of the user. The color of the measurement result screen D3 is gray, and the background of the display regions A31 to A38 is white. Therefore, the cross check mark CM is displayed with a color that calls the attention of the user in the measurement result screen D3, so that the user can easily recognize the cross check mark CM. If the display flag is set to "0" in the cross check set value database CB for all the cross check target items in which "1" is set to the cross check flag in the measurement result, the cross check mark CM described above is not displayed.

According to the above configuration, the user can freely set the cross check target item. For instance, the measurement value of the occult blood (BLD) of the urine qualitative measurement item and the measurement value of the red blood cells (RBC) of the urine sediment measurement item for the same sample are known to indicate a constant relationship. Thus, if the measurement value of the occult blood and the measurement value of the red blood cells are deviated from the constant relationship, whether the measurement result is accurate in either one of the measurement values is suspected. Therefore, the user sets the occult blood (BLD) and the red blood cells (RBC) as the cross check target items and appropriately sets the cross check table to cause the information processing unit 30 to determine whether or not the reliability of the measurement result is low.

The sample collected from the patient with early diabetic renal disease tends to demonstrate a high value in the cast (CAST) and also demonstrate a high value in the albumin/creatinine ratio (A/C). Therefore, the user sets the albumin/creatinine ratio (A/C) and the cast (CAST) for the cross check target items and appropriately sets the corresponding cross check table to cause the information processing unit 30 to perform the cross check of the measurement value of the albumin/creatinine ratio (A/C) and the measurement value of the cast (CAST). If the measurement value of the albumin/creatinine ratio (A/C) and the measurement value of the cast (CAST) conform to a predetermined relationship as a result of the cross check, the cross check target item name "A/C× CAST?" of the albumin/creatinine ratio (A/C) and the cast (CAST) is displayed in the display region A38 of the measurement result screen D3. If such cross check target item name "A/C×CAST?" is displayed, the user can recognize that early diabetic renal disease is suspected for the relevant sample.

The sample collected from the patient with chronic nephritis has a tendency of demonstrating high value for the protein (PRO) and high value also for the red blood cells (RBC). Therefore, the user sets the protein (PRO) and the red blood cells (RBC) for the cross check target items and appropriately sets the corresponding cross check table to cause the information processing unit 30 to perform the cross check of the measurement value of the protein (PRO) and the measurement value of the red blood cells (RBC). If the measurement value of the protein (PRO) and the measurement value of the red blood cells (RBC) conform to a predetermined relationship as a result of the cross check, the cross check target item name "PRO×RBC?" of the protein (PRO) and the red blood cells (RBC) is displayed in the display region A38 of the measurement result screen D3. If such cross check target item name "PRO×RBC?" is displayed, the user can recognize that chronic nephritis is suspected for the relevant sample.

The sample collected from the patient with chronic nephritis has a tendency of being "glomerular" in the red blood cell morphology information in addition to the above. Therefore, the user sets the protein (PRO) and red blood cell morphology information (RBC-Info.) for the cross check target item and appropriately sets the corresponding cross check table to cause the information processing unit 30 to perform the cross check of the measurement value of the protein (PRO) and the measurement value of the red blood cell morphology information (RBC-Info.). If the measurement value of the protein (PRO) and the measurement value of the red blood cell morphology information (RBC-Info.) conform to a predetermined relationship as a result of the cross check, the cross check target item name "PRO×RBC-Info.?" of the protein (PRO) and the red blood cell morphology information (RBC-Info.) is displayed in the display region A38 of the measurement result screen D3. If such cross check target item name "PRO×RBC-Info.?" is displayed, the user can recognize that chronic nephritis is suspected for the relevant sample.

The combination of the urine qualitative measurement item and the urine sediment measurement item used in the reliability determination of the measurement result or the clinical diagnosis differs depending on the medical facility (user) such as hospitals and test centers. In the urine sample testing apparatus 1 according to the present embodiment, the user can set the cross check target item in accordance with the standard of his/her facility since the user can freely set the cross check target item.

In the embodiment described above, the degree of freedom in the combination of the measurements when carrying out the check of the measurement result can be enhanced. The combination of the measurement items used to check the reliability of the measurement results thus can be easily extended as necessary. The information for assisting the diagnosis can be acquired from the measurement results of the two measurement items, so that the obtained measurement result can be utilized compared to one in the prior art.

Other Embodiments

The combination of the urine qualitative measurement item and the urine sediment measurement item typically used in the reliability determination of the measurement result or the like may be set in advance as a default value of the cross check target item. Therefore, when introducing the urine sample testing apparatus 1 in the user facility, the cross check of the measurement results can be carried out by the typically used cross check target item without setting the cross check target item, thereby alleviating the load of the user. After the urine sample testing apparatus 1 is introduced, the unique know-how of the reliability determination of the measurement result may be accumulated in the user facility, or the relationship of the measurement value of the urine qualitative measurement item and the measurement value of the urine sediment measurement item in a specific illness may be newly found, and then the user may set a unique cross check target item.

In the embodiment described above, a configuration of accepting the specification of both the urine qualitative measurement item and the urine sediment measurement item for the cross check target items in the cross check setting dialogue has been described, but this is not the sole case. A configuration of having a specific urine qualitative measurement item as a fixed set value, accepting the specification of the urine sediment measurement item corresponding to the urine qualitative measurement item, and setting the combination thereof as the cross check target item may be adopted, or a configuration of having a specific urine sediment measurement item as a fixed set value, accepting the specification of the urine qualitative measurement item corresponding to the urine sediment measurement item, and setting the combination thereof as the cross check target item may be adopted.

A configuration of displaying the combination of a plurality of urine qualitative measurement items and urine sediment measurement items on a screen with each combination being selectable, accepting the selection of the desired combination to be set as the cross check target item from the user, and setting the selected combination as the cross check target item may be adopted.

In the embodiment described above, a configuration in which the measurement unit 10 including the urine qualitative measuring section 11 and the urine sediment measuring section 12, and the information processing unit 30 are separately arranged, and the measurement unit 10 and the information processing unit 30 are communicably connected has been described, but this is not the sole case. A configuration in which the urine qualitative measuring section 11, the urine sediment measuring section 12, and the information processing unit 30 are mounted in one housing may be adopted.

In the above-described embodiment, a configuration of executing the setting of the cross check target item and the cross check of the measurement results by the information processing unit 30 of the urine sample testing apparatus 1 has been described, but this is not the sole case. A configuration in which the urine qualitative testing apparatus and a urine sediment testing apparatus are separately arranged, the cross check target item can be set in a urine sample test result processing apparatus where communicably connected to such apparatuses, the urine qualitative analysis result by the urine qualitative testing apparatus and the urine sediment analysis result by the urine sediment testing apparatus are received by the urine sample test result processing apparatus, and the cross check of the urine qualitative analysis result and the urine sediment analysis result is executed by the set cross check target item may be adopted.

What is claimed is:

1. A urine sample testing apparatus comprising:
   a urine qualitative measuring section configured to measure a urine sample and acquire a measurement result for each of a plurality of urine qualitative measurement items;
   a urine sediment measuring section configured to measure the urine sample and acquire a measurement result for each of a plurality of urine sediment measurement items;
   an operation part that is operable by a user to specify a combination of one of the plurality of urine qualitative measurement items and one of the plurality of urine sediment measurement items;
   an information processing unit configured to determine whether or not a first measurement result of the urine sample obtained by the urine qualitative measuring section and a second measurement result of the urine sample obtained by the urine sediment measuring section have a predetermined relationship with respect to the urine qualitative measurement item and the urine sediment measurement item included in the combination specified through the operation part; and
   an output unit configured to output a determination result by the information processing unit,
   wherein one of the plurality of urine qualitative measurement items is albumin/creatinine ratio,
   one of the plurality of urine sediment measurement items is cast, and
   the information processing unit accepts the specification of the combination of the albumin/creatinine ratio and the cast.

2. The urine sample testing apparatus of claim 1, wherein the operation part is operable by the user to select one measurement item from the plurality of urine qualitative measurement items with respect to a urine sediment measurement item, and/or the operation part is operable by the user to select one measurement item from the plurality of urine sediment measurement items with respect to a urine qualitative measurement item.

3. The urine sample testing apparatus of claim 2, wherein the output unit includes a display unit, and
the information processing unit is configured to show on the display unit an item setting screen, as the operation part, for specifying at least one measurement item from the plurality of urine qualitative measurement items and the plurality of urine sediment measurement items, and accept the specification of the combination through the item setting screen.

4. The urine sample testing apparatus of claim 3, wherein the item setting screen includes a first combination specifying portion for specifying a first combination of the urine qualitative measurement item and the urine sediment measurement item to be a target of the determination by the information processing unit, and a second combination specifying portion for specifying a second combination of the urine qualitative measurement item and the urine sediment measurement item to be a target of the determination by the information processing unit.

5. The urine sample testing apparatus of claim 4, wherein the item setting screen includes a first execution setting portion for setting whether or not to execute the determination by the information processing unit for the first combination, and a second execution setting portion for setting whether or not to execute the determination by the information processing unit for the second combination.

6. The urine sample testing apparatus of claim 3, wherein the item setting screen includes a first selecting portion for selecting one measurement item from the plurality of urine qualitative measurement items and a second selecting portion for selecting one measurement item from the plurality of urine sediment measurement items, and
the information processing unit accepts a combination of the measurement item selected by the first selecting portion and the measurement item selected by the second selecting portion as a target of the determination.

7. The urine sample testing apparatus of claim 3, wherein the item setting screen includes a first selecting portion for selecting one measurement item from the plurality of urine qualitative measurement items with respect to a predetermined urine sediment measurement item, and/or a second selecting portion for selecting one measurement item from the plurality of urine sediment items with respect to a predetermined urine qualitative item, and
the information processing unit accepts a combination of the measurement item selected by the first selecting portion and the predetermined urine sediment measurement item as a target of the determination, and/or accepts a combination of the measurement item selected by the second selecting portion and the predetermined urine qualitative item as a target of the determination.

8. The urine sample testing apparatus of claim 3, wherein the item setting screen includes a relationship setting portion for setting the predetermined relationship for the specified combination, the urine sample testing apparatus further includes a memory for storing the predetermined relationship set by the relationship setting portion, and the information processing unit determines whether or not the first measurement result and the second measurement result conform to the predetermined relationship stored in the memory.

9. The urine sample testing apparatus of claim 1, wherein the output unit outputs the measurement result for each of the plurality of urine qualitative measurement items of the urine sample and the measurement result for each of a plurality of urine sediment measurement items of the urine sample along with the determination result if determined by the information processing unit that the first measurement result and the second measurement result have the predetermined relationship.

10. The urine sample testing apparatus of claim 9, comprising an output mode setting part for setting an output mode of the determination result by the output unit.

11. The urine sample testing apparatus of claim 10, wherein the output mode setting part is configured to set whether or not to output a mark indicating that the first measurement result and the second measurement result have the predetermined relationship.

12. The urine sample testing apparatus of claim 1, wherein the information processing unit determines that the first measurement result and the second measurement result have the predetermined relationship when the first measurement result belongs in a first numerical range and the second measurement result belongs in a second numerical range associated with the first numerical range.

13. The urine sample testing apparatus of claim 1, wherein one of the plurality of urine qualitative measurement items is protein, one of the plurality of urine sediment measurement items is red blood cells or red blood cell morphology information, and the information processing unit accepts the specification of the combination of the protein and the red blood cells or red blood cell morphology information.

14. An apparatus for processing a measurement result of a urine sample comprising:

a measurement result acquiring unit configured to acquire a measurement result of a urine sample for each of a plurality of urine qualitative measurement items from a urine qualitative measuring section and acquire a measurement result of the urine sample for each of a plurality of urine sediment measurement items from a urine sediment measuring section;

an operation part that is operable by a user to specify a combination of one of the plurality of urine qualitative measurement items and one of the plurality of urine sediment measurement items;

an information processing unit configured to determine whether or not a first measurement result of the urine sample obtained by the urine qualitative measuring section and a second measurement result of the urine sample obtained by the urine sediment measuring section have a predetermined relationship with respect to the urine qualitative measurement item and the urine sediment measurement item included in the combination specified through the operation part; and an output unit configured to output a determination result by the information processing unit, wherein one of the plurality of urine qualitative measurement items is albumin/creatinine ratio, one of the plurality of urine sediment measurement items is cast, and the information processing unit accepts the specification of the combination of the albumin/creatinine ratio and the cast.

15. The apparatus of claim 14, wherein the operation part is operable by the user to select one measurement item from the plurality of urine qualitative measurement items with respect to a urine sediment measurement item, and/or the operation part is operable by the user to select one measurement item from the plurality of urine sediment measurement items with respect to a urine qualitative measurement item.

16. The apparatus of claim 15, wherein the output unit includes a display unit, and the information processing unit is configured to show on the display unit an item setting screen, as the operation part, for specifying at least one measurement item from the plurality of urine qualitative measurement items and the plurality of urine sediment measurement items, and accept the specification of the combination through the item setting screen.

17. The apparatus of claim 16, wherein the item setting screen includes a first combination specifying portion for specifying a first combination of the urine qualitative measurement item and the urine sediment measurement item to be a target of the determination by the information processing unit, and a second combination specifying portion for specifying a second combination of the urine qualitative measurement item and the urine sediment measurement item to be a target of the determination by the information processing unit.

18. The apparatus of claim 17, wherein the item setting screen includes a first execution setting portion for setting whether or not to execute the determination by the information processing unit for the first combination, and a second execution setting portion for setting whether or not to execute the determination by the information processing unit for the second combination.

19. The apparatus of claim 16, wherein the item setting screen includes a first selecting portion for selecting one measurement item from the plurality of urine qualitative measurement items and a second selecting portion for selecting one measurement item from the plurality of urine sediment measurement items; and the information processing unit accepts the combination of the measurement item selected by the first selecting portion and the measurement item selected by the second selecting portion as the target of determination.

* * * * *